(12) United States Patent
Salehpoor

(10) Patent No.: US 6,723,132 B2
(45) Date of Patent: Apr. 20, 2004

(54) ARTIFICIAL LUNG DEVICE

(76) Inventor: Karim Salehpoor, 10212 Coronado Ave., NE., Albuquerque, NM (US) 87122

(*) Notice: Subject to any disclaimer, the term of this patent is extended or adjusted under 35 U.S.C. 154(b) by 23 days.

(21) Appl. No.: 10/179,309

(22) Filed: Jun. 26, 2002

(65) Prior Publication Data

US 2004/0002771 A1 Jan. 1, 2004

(51) Int. Cl.$^7$ .................................................. A61F 2/36
(52) U.S. Cl. ............................... 623/23.65; 128/200.24
(58) Field of Search .................. 623/23.65; 128/200.24, 128/205.27, 205.28; 604/6.14; 422/44, 45

(56) References Cited

U.S. PATENT DOCUMENTS

| 4,188,360 A | 2/1980 | Kurata |
| 4,231,988 A | 11/1980 | Kurata |
| 4,239,729 A | 12/1980 | Hasegawa et al. |
| 4,376,095 A | 3/1983 | Hasegawa |
| 4,650,457 A | 3/1987 | Morioka et al. |
| 5,034,188 A | 7/1991 | Nakanishi et al. |
| 5,084,244 A | 1/1992 | Muramoto |
| 5,192,320 A | 3/1993 | Anazawa et al. |
| 5,263,982 A | 11/1993 | Shimomura et al. |

FOREIGN PATENT DOCUMENTS

| GB | 1 415 946 | 12/1975 |
| GB | 2 082 475 A | 3/1982 |
| JP | 409108337 A | 4/1997 |
| JP | 411146915 A | 6/1999 |

*Primary Examiner*—Corrine McDermott
*Assistant Examiner*—William H. Matthews
(74) *Attorney, Agent, or Firm*—Richard C. Litman

(57) ABSTRACT

An artificial lung for humans and other mammals inserted within the body or placed externally. The artificial lung comprises an electrically actuated three-way valve, a casing containing parallel loops of oxygenator tubes for oxygenation of blood by an atmosphere of circulating air, and an air circulation driving fan powered by an energizing system. As a safety factor in the event of leakage in the casing, a check valve is inserted in an effluent blood duct from the casing to the aerated effluent blood. Two artificial lungs can be utilized internally as left and right lungs.

10 Claims, 2 Drawing Sheets

ARTIFICIAL LUNG DEVICE

BACKGROUND OF THE INVENTION

1. Field of the Invention

The present invention relates generally to lung aids. More specifically, the invention is an artificial lung for humans and other mammals, and either inserted within the body (with internal energizing system) or placed externally and energized by battery or batteries, or an A.C. source.

2. Description of the Related Art

The related art describes various artificial lung apparatus, but none discloses the present invention. There is a need for an effective and economical artificial lung which actually replaces an organic lung in humans and other mammals with the dual capability of either being inserted within the body or positioned outside the body. The electrical power is supplied by an energizing system.

The related art of interest will be discussed in the order of perceived relevance to the present invention.

U.S. Pat. No. 5,192,320 issued on Mar. 9, 1993, to Takanori Anazawa et al. describes a membrane-type artificial lung adapted to perform an exchange of gases between blood and an oxygen-containing gas through a membrane by passing blood over one side of the membrane and either oxygen or an oxygen-containing gas over the other side. The membrane is a hollow fiber membrane which is composed mainly of polyolefin, and has an inside diameter of 10 to 500 micrometers, a thickness of 5 to 100 micrometers, a porosity of 7–50%, an oxygen flux of at least $1 \times 10^{-6}$ [$cm^3$ (STP)/$cm^2$.sec.cm Hg)], and is substantially impermeable to ethanol. Hollow fiber membranes are made from either poly(4-methylpentene-1), silicone, or polypropylene. In the intracapilliary blood flow mode, the artificial lung has 1,000 to 100,000 hollow fibers in a cylindrical shape of a diameter of 25 cm. and a length not more than 30 cm. When the artificial lung is used as an extracapillary blood flow mode, the lung includes 1,000 to 60,000 hollow fibers with a diameter of 20 cm. and a length not more than 30 cm. The lung device is distinguishable for requiring a large number of fibers and a large size.

U.S. Pat. No. 4,231,988 issued on Nov. 4, 1980, to Motoji Jurata describes an artificial lung comprising two oxygen blowing stages in an upright cylindrical housing containing a plurality of oxygenation tubes arranged coaxially, and including defoaming means. The device is distinguishable for requiring two oxygenation stages and a defoaming means.

U.S. Pat. No. 4,650,457 issued on Mar. 17, 1987, to Tohru Morioka et al. describes an apparatus for extracorporeal assistance including a pump device having a flexible blood reservoir housed in a rigid housing. The pump expands and contracts the blood reservoir to repeat cycles of blood feed and blood take-off. A membrane artificial lung is included at the end to feed oxygenated blood via a catheter to the patient. The membrane artificial lung may be coil type, plate type, or of hollow fiber type which is preferred. The membrane may be a silicone polymer membrane, or a porous membrane of polypropylene, polyethylene, polytetrafluoroethylene, or polysulfone alone or filled with silicone oil. The lung device containing system is distinguishable for requiring a pump.

U.S. Pat. No. 5,263,982 issued on Nov. 23, 1993, to Yasushi Shimomura et al. describes a hollow fiber membrane type artificial lung comprising a cylindrical casing having an upper head cap with a fresh air inlet and an oxygenated blood outlet. The lower head cap has a centered duct for receiving blood and an outlet for oxygenated air. The hollow fibers are collected either in parallel or twilled, wherein one fiber passes over one fiber and over two or more warp fibers to give the appearance of diagonal lines. One fiber or 2 to 20 fibers with preferably 4 to 6 fibers can be used by forming on a collecting rod later removed. Polypropylene fibers are preferred, but polyethylene, polytetrafluoroethylene, polysulfon, polyacrylonitrile, polyurethane, and silicon can be used. The fibers can be porous (0.01 to 1 micron diameter pores) or non-porous. The device is distinguishable for requiring a centered channel in the twilled fibers.

U.S. Pat. No. 4,239,729 issued on Dec. 16, 1980, to Hiroshi Hasegawa et al. describes a blood oxygenator device comprising a cylindrical housing provided with inlet and outlet ports for oxygen, and a bundle of hollow fibers inside arranged in parallel and axially. A second embodiment has a fastened mid-portion aided by a circular inward projection. The porous hollow fibers are made of polyolefin resin, sized at 100 to 300 microns in inner diameter and 10 to 50 microns in wall thickness, and have an average pore size of 200 to 1,000 Angstroms and porosity of 20 to 80%. The blood oxygenator device is distinguishable for being limited to the oxygenator housing.

The following six patents require a heat exchanger in their artificial lung devices, which heat exchanger is not required in the present invention.

U.S. Pat. No. 5,034,188 issued on Jul. 23, 1991, to Hikaru Nakanishi et al. describes an artificial lung comprising a venous blood reservoir to receive and store venous blood which is passed through a heat exchanger to a blood oxygenator concentrically arranged within the heat exchanger. The hollow fibers are spirally wound to form a plurality of bundle layers. The device is distinguishable for requiring blood storage, a heat exchanger, a concentrically arranged blood oxygenator, and an external pump.

U.S. Pat. No. 4,376,095 issued on Mar. 8, 1983, to Hiroshi Hasegawa describes a hollow fiber-type artificial lung device having two adjacent housings for a hollow fiber bundle followed by a heat exchanger. The device is distinguishable for requiring an integrated downstream heat exchanger.

U.S. Pat. No. 5,084,244 issued on Jan. 28, 1992, to Tomonori Muramoto describes an artificial lung assembly comprising a two-piece cylindrical housing of a combined heat exchanger unit and oxygenator unit used for treating blood from a patient. The lower oxygenator unit utilizes straight conventional hollow fibers positioned in parallel. The device is distinguishable for requiring a heat exchanger for heating the incoming blood.

U.S. Pat. No. 4,188,360 issued on Feb. 12, 1980, to Motoji Kurata describes an artificial lung with a built-in heat exchanger comprising an outer cylindrical housing, an inner cylindrical member, and a shortened intermediate member. A plurality of tubes are disposed axially within the inner cylindrical element through which a heat exchange medium is circulated. The oxygenation is carried out in the inner cylindrical member while heat exchange is performed between the blood and the heat exchange medium. The device is distinguishable for the physical structure and the requirement of an integrated heat exchanger structure.

U.K. Patent Application No. GB 2 082 475 A published on Mar. 10, 1982, for Juro Wada et al. describes an artificial lung device comprising the direction of venous blood to a reservoir by filtering and pumping. The blood is pumped sequentially to a heat exchanger, an artificial lung, a second reservoir tank, a second blood pump, and filter before returning to the patient. Water from the blood is removed between the oxygenator and the reservoir tank. The oxygenator utilizes polyacrylonitrile type membranes. The system is distinguishable for requiring various pumps and a heat exchanger.

U.K. Patent Application No. 1 415 946 published on Dec. 3, 1975, for Rhone-Poulenc, S. A. describes an artificial lung device used in a first chamber of a two-chamber system. The second chamber is an air conditioning device to bring air to a desired temperature and degree of humidity. Pumps feed the incoming blood and treated blood. A third vacuum pump is required for recycling air and discarding a bleed-off to the atmosphere. Other elements of the air treatment system require in sequence pure compressed oxygen, a gas injector, flow meters, a soda-lime purifier element, and a mixer element. The system is distinguishable for requiring pure oxygen, a gas ejector, a soda-lime treatment, and conditioning of the air intake.

Japan Patent Application No. 409-108337 published on Apr. 28, 1997, for Mitsuaki Ogiwara et al. describes an external pressure control valve for an artificial lung device which lowers the pressure inside the oxygenator cylinder lower than ambient pressure by operating a suction device. The valve is distinguishable in that the present invention does not require it, but an electrically actuated three-way valve to control flow to three different elements.

Japan Patent Application No. 11-146915 published on Jun. 2, 1999, for Hideto Kaneyasu describes an external circulating type cardiorespiration auxiliary device requiring an artificial respiratory apparatus used as the blood pump driving source simultaneously with the oxygen added mixed gas source. The device is distinguishable for using the oxygenator device for two different processes.

None of the above inventions and patents, taken either singularly or in combination, is seen to describe the instant invention as claimed. Thus, an artificial lung device solving the aforementioned problems is desired.

SUMMARY OF THE INVENTION

The invention is an artificial lung for humans and other mammals having the versatility and capability of being inserted either within the body or placed externally, and energized by batteries or an A.C. source. The artificial lung has four basic elements: 1) a blood compartment integrated with 2) an air compartment in a casing, 3) a fan, and 4) an electrically actuated three-way valve. The blood flows under its own pressure through parallel fiber tube banks made of a conventionally obtained membrane oxygenator material housed in the air compartment of the casing. The fan draws fresh air into the air compartment at a distal end by exhausting air from the proximate end of the air compartment. The electrically actuated three-way valve controls the proper time interval for air flow during the inspiration and expiration processes of a breathing cycle. In the inspiration process the valve permits the fan to draw in fresh air into the air compartment in order for the oxygen in the air to enter the membrane oxygenator element and the blood stream, and the carbon dioxide to exit the blood stream and enter the air stream. In the expiration process, the electrically actuated three-way valve permits the fan to force the carbon dioxide out of the air compartment. A check valve is inserted in an effluent air duct joining the effluent blood containing duct exiting the blood compartment of casing. This artificial lung can completely replace a natural lung without creating an acid-base disturbance in the blood.

Accordingly, it is a principal object of the invention to provide an artificial lung for humans and other mammals.

It is another object of the invention to provide an artificial lung which can be positioned inside or outside the body.

It is a further object of the invention to provide an artificial lung including fiber tube banks made from membrane oxygenator material housed in an air compartment.

Still another object of the invention is to provide an electrically actuated three-way valve and a fan for controlling the proper timing and flow, respectively, for air flow during inspiration and expiration of air.

Yet another object of the invention is to provide a check valve in an effluent air duct exiting from the casing to join the effluent aerated blood duct going to the patient.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
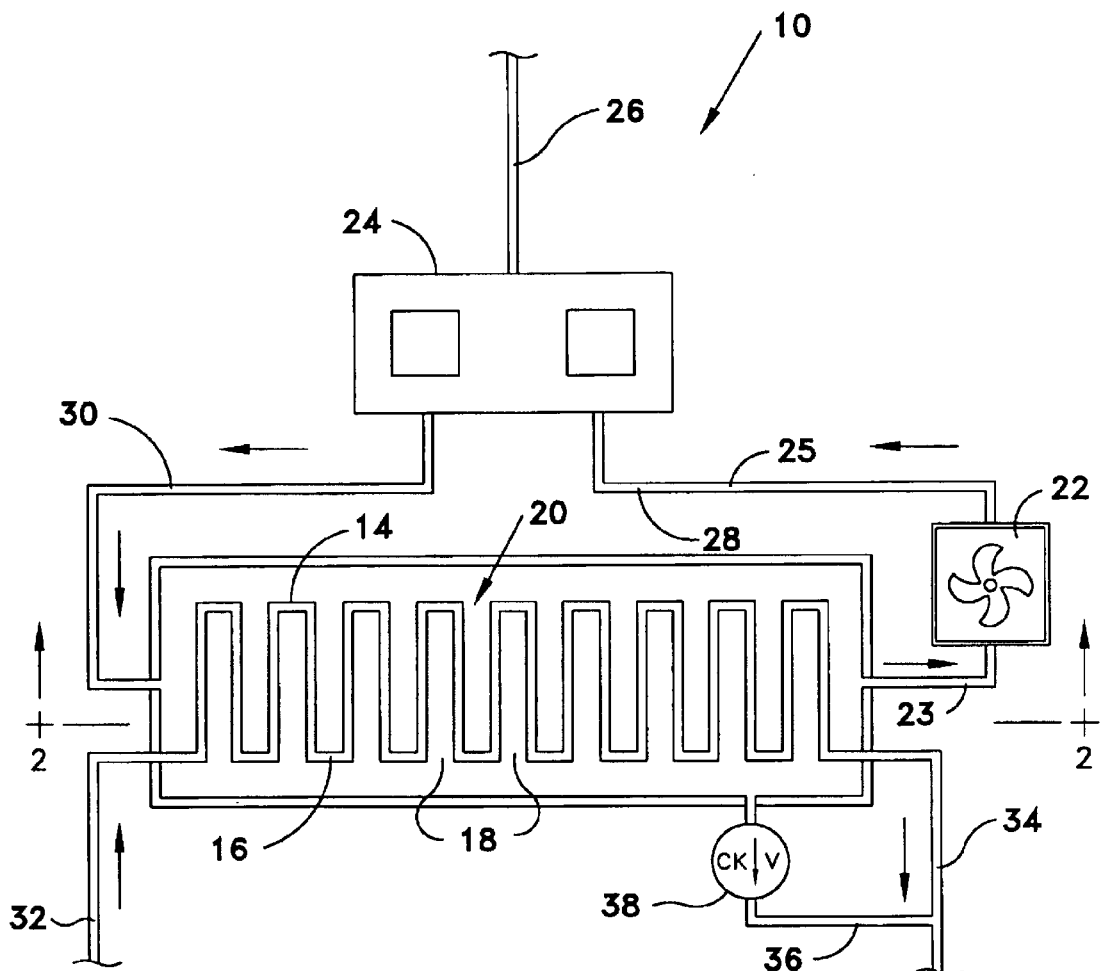
FIG. 1 is a schematic view of an artificial lung device according to the present invention.
Figure 2:
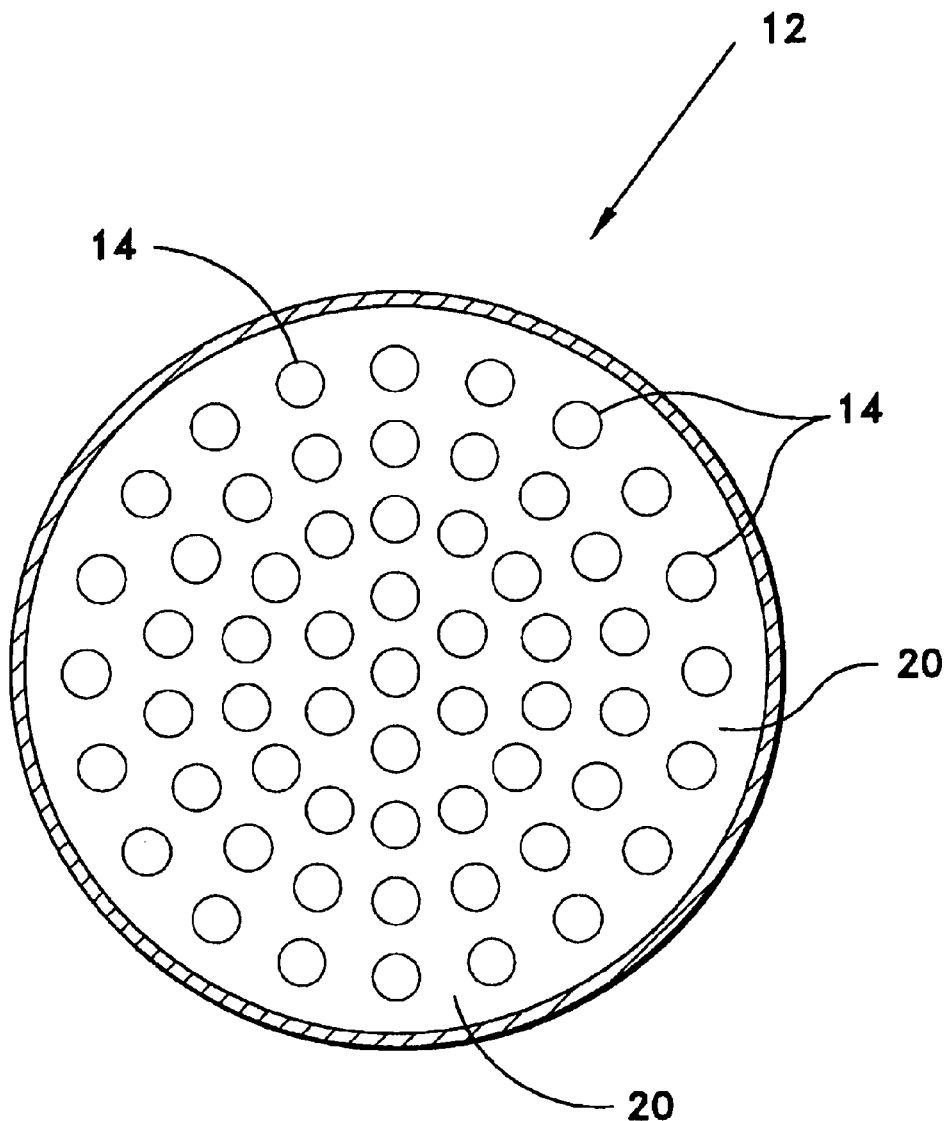
FIG. 2 is a diagrammatic cross-sectional view 2—2 of the blood and air compartments in the artificial lung device according to the present invention.

The present invention illustrated in FIG. 1 is drawn to an artificial lung device 10 comprising a cylindrical metal or non metal casing 12 containing parallel loops of oxygenator tubes or fibers 14 for flowing blood 16 separated by an air compartment spacing 18 which provides the circulation of air 20. FIG. 2 is a schematic cross-sectional illustration of the spacing of the oxygenator tubing or fibers 14 within the casing 12. The spaced tubing or fiber 14 can be grouped in a bundle at both ends. The spaced tubing or fibers 14 can be formed in a spiral or aligned in parallel.

A miniature fan 22 extracts effluent air from the casing 12 via tubing 23, and propels the carbon dioxide (or poor oxygen air) 28 to the trachea via tubing 25, an electrically actuated three-way valve body 24 equipped with an electrical actuator and an energizing system (not shown), a tube 26, and a conventional plastic (preferred) or metal coupling (not shown). A tube 30 from the three-way valve body 24 feeds fresh influent air to the casing 12.

The electrically actuated three-way valve 24 controls the proper time interval for flow of richly oxygenated air and poorly oxygenated air during the inspiration and expiration processes. In the inspiration process, the electrically actuated three-way valve is in a 1-2 position where the fan 22 draws fresh air into the air compartment to enable oxygen to enter the passing blood stream 16 and carbon dioxide enters the air stream 20. In the expiration process, the electrically actuated three-way valve body 24 is in the 1-3 position where the fan blows the carbon dioxide (or oxygen-deficient air) out of the air compartment 18.

Duct 32 is connected to the pulmonary artery (arteries) by conventional plastic (prefer-red) or metal coupling(s) (not shown) and distributes the oxygen deficient blood to the parallel banks of oxygenator fibers 14 housed in the casing 12. Duct 34 collects the oxygenated blood from the banks of oxygenator fibers 14 and delivers it to the pulmonary vein(s) via conventional plastic (preferred) or metal coupling(s) (not shown). As a safety factor, a plastic tube 36 with a plastic (preferred) check valve 38 (FIG. 1) connects the bottom of casing 12 to duct 34 to redirect any accumulated blood inside casing 12, due to possible leakage from the fiber bank 14, into the patient's venous system.

The entire system except the couplings is encased in a liquid-proof plastic container (not shown) for insertion within a mammalian body or positioned outside the body for oxygenation of blood and return of the blood to the mammalian body.

Exemplary dimensions of the elements required in the invention are as follows. The plastic ducts 32 and 34 have an inside diameter of approximately 1 inch. Plastic tubing 26 has an inside diameter of approximately 1 inch. Plastic tubings 23, 25 and 30 have an inside diameter of approximately 0.5 inch. The oxygenator tubing or fibers 14 may have an inside diameter of approximately 100 to 500 microns. The electrically actuated three-way valve body 24 is approximately 1 inch by 1 inch by 2 inches. The check valve 38 and its tubing is 0.125 inch.

Thus, the artificial lung device 10 can completely replace a natural lung either externally or within the body by adding one (or two devices to serve as internal right and left lungs) without creating an acid-base disturbance in the blood stream outside the lungs.

The device 10 can be applied in hospitals during surgery. Previously invented oxygenator devices are inserted in the blood stream to oxygenate the blood before it enters the lungs to help natural lungs. However, oxygenating the blood before it enters natural lungs creates an acid-base disturbance in the blood stream, which disturbance disrupts the normal functioning of the natural lung. The artificial lung device 10 is also economical to produce and install.

It is to be understood that the present invention is not limited to the embodiments described above, but encompasses any and all embodiments within the scope of the following claims.

I claim:

1. An artificial lung device comprising:
   a cylindrical metal or plastic casing containing parallel loops of oxygenator tubes for flowing blood separated by a spacing;
   said spacing providing circulation of air;
   a miniature enclosed fan for exhausting effluent air from said casing and intake of fresh air to said casing; and
   an electrically actuated three-way valve structured and arranged for connection to the trachea by a tube and a coupling, and receiving the effluent air from the fan, and a tube from the electrically actuated three-way valve feeding fresh air to the casing;
   said casing, fan and electrically actuated three-way valve is encased in a liquid-proof bag that is structured and arranged for insertion within a mammalian body or is positioned outside the mammalian body for oxygenation of blood and is structured and arranged to return the blood to the mammalian body.

2. The artificial lung device according to claim 1, wherein the electrically actuated three-way valve receives exhaust air from the miniature enclosed fan via a duct.

3. The artificial lung device according to claim 1, wherein the cylindrical casing has an effluent duct connected to the exhaust fan.

4. The artificial lung device according to claim 1, wherein the electrically actuated three-way valve has an effluent duct structured and arranged for connection to the trachea of the mammalian body.

5. The artificial lung device according to claim 1, wherein the electrically actuated three-way valve has an effluent duct structured and arranged for connection to the cylindrical casing.

6. The artificial lung device according to claim 1, wherein the cylindrical casing has a influent duct connecting loops of oxygenator fibers to pulmonary arteries of the mammalian body.

7. The artificial lung device according to claim 1, wherein the cylindrical casing has a first effluent duct connecting loops of oxygenator fibers structured and arranged for connection to pulmonary veins of the mammalian body.

8. The artificial lung device according to claim 7, wherein the cylindrical casing bottom has a second effluent duct for collecting any blood leakage, and is connected to the first effluent duct that is structured and arranged for connection to the pulmonary veins of the mammalian body.

9. The artificial lung device according to claim 8, wherein the second effluent duct has a check valve.

10. The artificial lung device according to claim 8, wherein two artificial lung devices are used in parallel.

* * * * *